United States Patent [19]

Dewaele

[11] Patent Number: 5,832,055
[45] Date of Patent: Nov. 3, 1998

[54] METHOD OF CORRECTING A RADIATION IMAGE FOR DEFECTS IN THE RECORDING MEMBER

[75] Inventor: Piet Dewaele, Berchem, Belgium

[73] Assignee: Agfa-Gevaert, Mortsel, Belgium

[21] Appl. No.: 906,704

[22] Filed: Aug. 6, 1997

[30] Foreign Application Priority Data

Aug. 8, 1996 [EP] European Pat. Off. .............. 96202232

[51] Int. Cl.$^6$ ................................................. G01N 23/04
[52] U.S. Cl. ............................................. 378/62; 250/587
[58] Field of Search ................................... 250/582, 587; 378/62, 207

[56] References Cited

U.S. PATENT DOCUMENTS

| | | | |
|---|---|---|---|
| 4,611,283 | 9/1986 | Lumelsky et al. | 250/363.07 |
| 5,151,596 | 9/1992 | Saotome | 250/585 |
| 5,231,574 | 7/1993 | Agano | 382/132 |
| 5,565,678 | 10/1996 | Manian | 250/252.1 |
| 5,633,510 | 5/1997 | Rogers | 250/587 |

FOREIGN PATENT DOCUMENTS

| | | |
|---|---|---|
| 0238962 | 3/1987 | European Pat. Off. . |
| 0574969 | 5/1993 | European Pat. Off. . |

*Primary Examiner*—David P. Porta
*Assistant Examiner*—David Vernon Bruce
*Attorney, Agent, or Firm*—Baker & Botts, L.L.P.

[57] ABSTRACT

Method of correcting a radiation image for defects in the recording member. Defects in a member for recording a radiation image are corrected by generating a calibration matrix comprising for each pixel a correction value and by applying corresponding elements of the calibration matrix to the pixels of a recorded image. The values of the calibration matrix represent in each pixel the deviation of the value that is effectively obtained in a pixel when the recording member is subjected to a flat field exposure and the value that would be expected in the pixel. Different methods are described for determining the expected value in a pixel. Further, an overlay image is generated wherein local defects are visualised.

21 Claims, 9 Drawing Sheets

| 0.0025 | 0.0125 | 0.02 | 0.0125 | 0.0025 |
|--------|--------|------|--------|--------|
| 0.0125 | 0.0625 | 0.1  | 0.0625 | 0.0125 |
| 0.02   | 0.1    | 0.16 | 0.1    | 0.02   |
| 0.0125 | 0.0625 | 0.1  | 0.0625 | 0.0125 |
| 0.0025 | 0.0125 | 0.02 | 0.0125 | 0.0025 |

METHOD OF CORRECTING A RADIATION IMAGE FOR DEFECTS IN THE RECORDING MEMBER

FIELD OF THE INVENTION

The present invention is in the field of medical imaging. The invention more specifically relates to the detection and locating of defects of any type and size in a recording member for storing a radiation image. The invention further relates to the correction of such defects in a radiation image.

DESCRIPTION OF THE STATE OF THE ART

In the field of digital medical imaging a wide variety of image acquisition techniques have been developed that render a digital representation of a medical image.
Among such techniques are computerised tomography, nuclear magnetic resonance, ultrasound, detection of a radiation image by means of a CCD sensor or a video camera, radiographic film scanning, techniques using Selenium and a read-out system such as thin film transistors etc.

In still another technique, X-rays transmitted by an exposed object (such as the body of a patient) are stored in a photostimulable phosphor screen. Such a photostimulable phosphor screen comprises a layer of photostimulable luminescent material which comprises a phosphor, for example a europium-activated barium fluoro-halide, and a binder. The phosphor has the characteristic that it can be energised to an excited state by X-rays, and can then be stimulated by light within a first wavelength range to return to the ground state with the emission of light within a second wavelength range. The stimulating radiation is arranged to have a different wavelength from the emitted light. With regard to the specific example wherein a radiation image is stored in a screen comprising a europium-activated barium fluoro-halide phosphor, the stimulating light is situated within the range of 600–700 nm and the emitted light is situated within the range of 350–450 nm.

In order to read the image stored in an exposed screen, the screen is transported past a scanning station where it is two-dimenstionnally scanned with stimulating light. For this purpose a light beam of a wavelength within the stimulating wavelength range of the phosphor is deflected so as to scan the screen in a first direction (called main scan direction) while it is transported in a second direction that is perpendicular to the main scan direction.

Light emitted upon stimulation is guided through a light guide member onto an opto-electric transducer such as a photomultiplier that converts the emitted light into a corresponding analog electric signal. This analog electric signal is then converted into a digital image signal by means of an A/D converter.

A digital image representation acquired through the use of a photostimulable phosphor screen as an intermediary storage means or a digital image representation acquired by any other kind of detector and/or image acquisition system, always comprises noise to some extent.

Especially in the field of medical imaging wherein systems are developed for extracting information from a patient's body and for presenting this information to a physician to allow him to perform a diagnosis, it is extremely important that all imaging defects in the image are detected and signalled since they may interfere with relevant signal components and may as such have an influence on the diagnosis.

The present invention deals in particular with the detection of defects on the digital image representation of a medical radiation image. Still more specifically the present invention deals with defects on a radiation image that is stored in a photostimulable phosphor screen that is read out according to the above described read-out process.

Defects on a stimulable phosphor may originate from several causes. In the context of the present invention, these defects may be classified into three classes: (1) point defects originating from grain size impurities in the moulding process of the phosphor screen, or from dust during subsequent use. The spatial dimension of point defects is small with respect to both principal image dimensions, their gray value amplitude exceeds the imaging chain noise amplitude in a case-dependent extent. (2) line-like or curve-like defects, originating either from smear during the production process or from mechanical wear during use. These class of defects may further be subdivided by (a) pure line defects such as—but not limited to—produced by mechanical rollers; (b) scratches due to e.g. handling and damage; (c) curve-like defects due to any kind of one-dimensional distortion process. All of these subclasses of linear defects has large ratio of length along the axis of the defect w.r.t. the across dimension; the amplitude can vary widely, the weakest amplitude (as produced by e.g. smear) being considered unacceptable. (3) area defects such as spots, and global impurities e.g. coming from the moulding process at production or moisture during use. This class of defects shows dimensions in either of the principal image axes. Still further causes of sources of defects may be thought of, but the shape of any of the resulting defects can always be classified as either a point, a line or an area defect. A common characteristic shared by of all of the aforementioned classes of defects is that they may be present already at fabrication time or come into being during use of the imaging plate. This fact necessitates the periodical inspection of imaging plates to detect the presence of (newly) appeared defects, at regular intervals of the life time of the plate.

The early interception of these defects and the subsequent corrective action is indicated at least in the production stage and is particularly motivated during use in critical application areas such as mammography. Regular screening of the total installed base of imaging plates as to the presence of any of the mentioned defects is mandatory. This kind of quality control is commonly known as visual inspection. Human inspectors, however, are subject to subjective perception and assessment. Moreover, the presence of subtle abnormalities such as dust, small scratches and global impurities may be poorly detectable or even remain unnoticed. However, these defects leave a clearly visible imprint in the digital image, and may severely impair correct diagnosis by the radiologist. Dust and scratches could possibly be confused with potential microcalcifications on digitized or digital mammograms. Mammography is a typical application area requiring the highest image quality standards available. The field of research aiming at developing automatic detection methods for any of these defects by computerized inspection is commonly known as automatic visual inspection.

The result of the automatic visual inspection may either be (1) the complete rejection of an imaging plate due to an unacceptable defect, according to a quantifiable measure or (2) the marginal acceptance of the imaging plate with signalling and indication of zones requiring special attention or (3) acceptance of the image plate.

Automatic visual inspection is a well developed field in digital image processing, such as presented in the F. van der Heijden, Image based measurement systems, Wiley, 1994. However, very little mention is made in the literature of methods applicable to the highly specialized area of film inspection and phosphor imaging plate inspection.

In P. Dewaele et al., An application of the Lily software package to defect inspection in unexposed radiographic film, Proc. of the SPIE, The Sixth Meeting in Israel on Optical Engineering, Vol. 1038, Dec. 1988, pure one-dimensional techniques based on edge and level measures are developed for fast on-line inspection of radiographic film. However, they assume linear defects in the along direction only. Automated inspection of phosphor plate has to cope with a much wider variety of defect geometry, necessitating the use of two-dimensional techniques. Currently, inspection of phosphor imaging plates is done manually and on a representative sample of a production batch. However, in view of the benefits given before, an automatic inspection is highly desirable.

OBJECTS OF THE PRESENT INVENTION

It is a primary object of the present invention to provide a method to detect and locate point, line and area defects of a recording member in which a radiation image is stored, and to assess the degree of severity, to delineate the region of support of the defect and to correct an actual radiation image for these defects.

It is a further object to provide an accompanying overlay image showing the defective zones on the recording member requiring specific clinician's attention, and to provide a two-dimensional calibration matrix supplying correction factors to correct a registered actual image on a pixel-by-pixel basis.

Still further objects will become clear from the description given hereafter.

SUMMARY OF THE INVENTION

The objects of the present invention are achieved by a method of correcting a radiation image stored in a recording member for recording member defects comprising:

generating a calibration matrix for a recording member, said calibration matrix comprising for each pixel on said recording member a correction value that represents the deviation of the value that is effectively obtained in a pixel and a value that would be expected, when said recording medium is subjected to a flat field exposure and subsequently read-out by means of a calibrated read-out system, generating a digital signal representation of the radiation image by reading the image by means of a calibrated read-out system, correcting each pixel of said radiation image by applying to a pixel a corresponding value of said calibration matrix.

A calibration matrix is generated as follows:

first the recording member is exposed to a flat field exposure of radiation, next the image stored in the recording member that has been exposed to the flat field exposure is read-out with a calibrated read-out system (so that influences on the read-out signal that do not originate from a defect in the read-out member are eliminated)

next pixel values of the flat field image are averaged to generate an average value of $\mu_R$, then a smooth background image $g_R(i,j)$ is calculated by one of the methods described below, finally the values of the calibration matrix are calculated either as $\mu_R - g_R(i,j)$ in the additive case wherein pixel values of the radiation image are corrected by adding to a pixel value a corresponding value of the calibration matrix, or as $\mu_R/g_R(i,j)$ in the multiplicative case wherein pixel values of the radiation image are corrected by multiplying a pixel value of the radiation image with a corresponding value of the calibration matrix.

The generation of the calibration matrix and in particular alternative methods for the generation of the background image will be explained below in more detail.

In the context of the present invention the term 'radiation' refers to penetrating radiation of any kind such as X-rays, gamma rays etc.

A recording member in the context of the present invention is a member wherein a radiation image, for example an X-ray image, can be temporarily or definitely stored. Different types of recording media may be used. One example of a reusable recording member is a photostimulable phosphor screen. An example of a non-reusable member is a radiographic film. Still others may be envisaged, such as different screen-film combinations.

By means of the term 'flat field exposure' is meant a uniform exposure of the recording member to penetrating radiation so that ideally in every pixel of a defectless recording member an identical value would be read-out when using an optimally calibrated read-out system.

A calibrated read-out system is a system that has been corrected for any non-uniformities in the read-out signal that originate from the system's components itself.

Causes for such non-uniformities can for example be attributed to the means for directing light onto an opto-electric transducer. These phenomena as well as examples of adequate correction methods have been described in extenso in the state of the art literature, for example in U.S. Pat. No. 4,885,467 and in Research Disclosure N 352, page 484–485 (1993).

The term 'corresponding' refers to corresponding elements in the actual image and the calibration matrix, both being brought in the register as explained furtheron.

BRIEF DESCRIPTION OF THE DRAWINGS

Particular embodiments of the invention will now be explained in more detail with reference to the accompanying drawings wherein FIG. 1 generally illustrates an apparatus for reading out a photostimulable phosphor screen, FIG. 2 schematically illustrates the method of the present invention.

The method of the present invention will be explained in general with reference to FIG. 2. The part relating to the acquisition of the digital signal representation of a radiation image is illustrated in FIG. 1 for a specific example wherein a radiation image is stored in a photostimulable phosphor screen.

Figure 1:
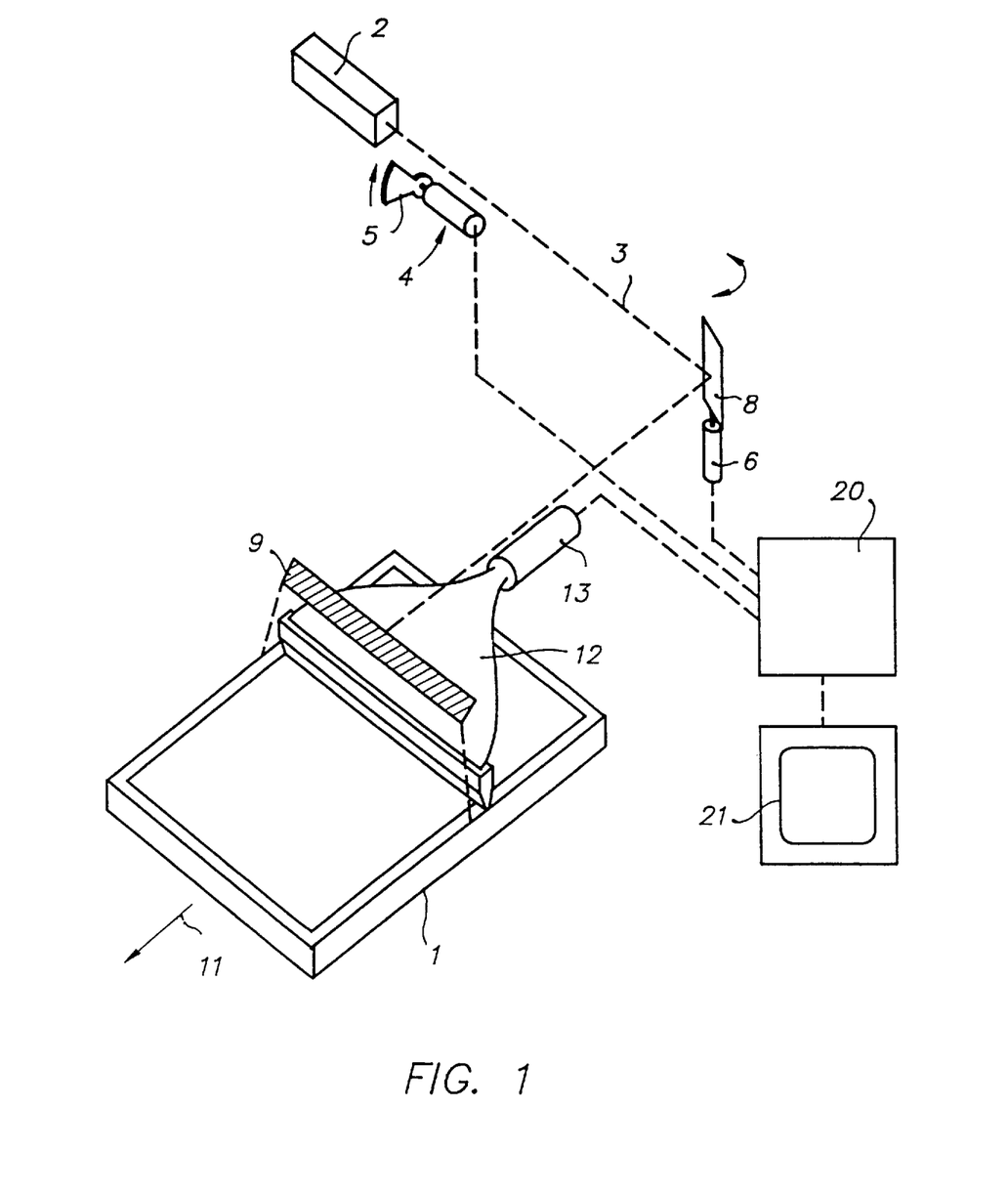
Figure 2:
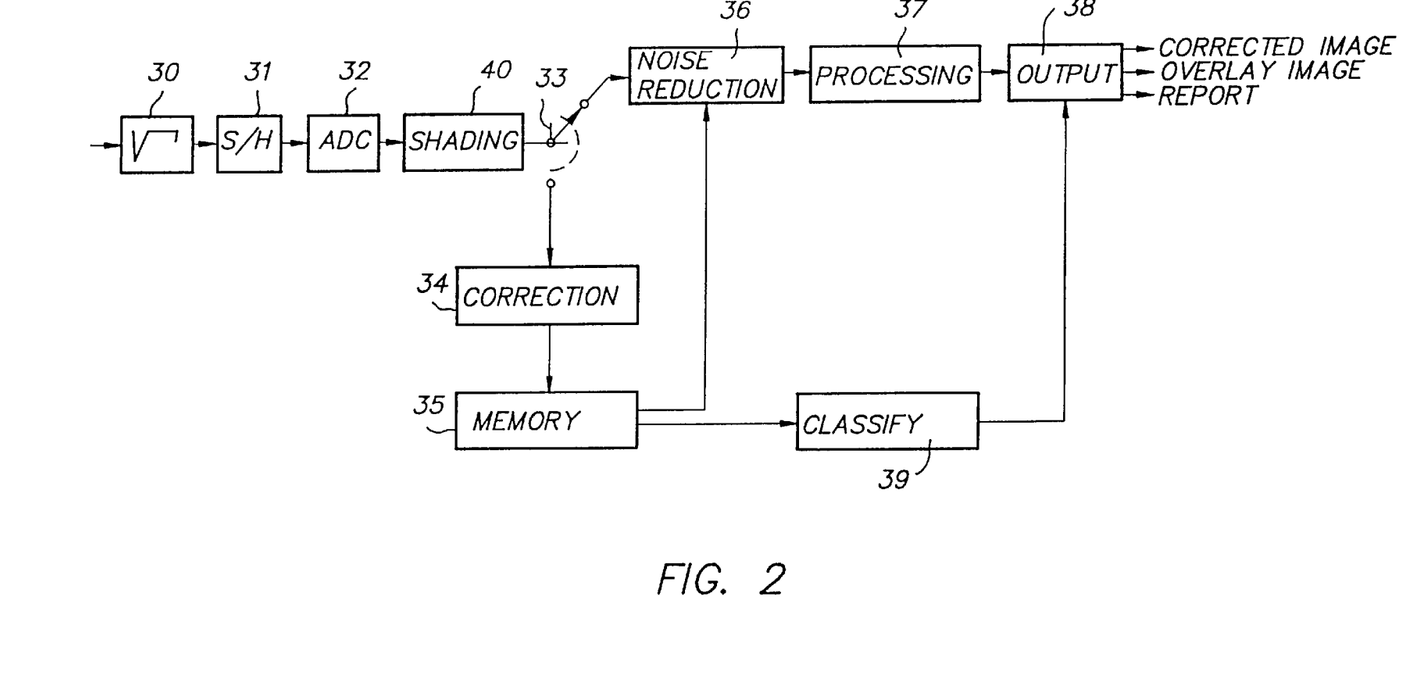

After a stimulable phosphor sheet 1 is exposed to radiation, such as to X-rays, passing through an object to have a radiation image stored thereon, it is sent to the read-out station shown in FIG. 1. A laser beam 3, having a wavelength of 633 nm, is emitted from a helium-neon laser source 2, and directed towards a galvanometer mirror 8. Drive means 6 cause the galvanometer mirror to reciprocate in a triangular wave pattern. A light chopper 4, including a rotating disc segment 5, is positioned to enable the disc segment to interrupt the laser beam pathway during the galvanometer retrace step.

Various laser beam focusing devices, known in the art, not shown in the drawings, ensure a uniform beam diameter during scanning of the beam on the phosphor sheet and also ensure that the uniform angular velocity of the reciprocating mirror 8 results in the laser spot travelling across the phosphor sheet at a uniform linear speed. The laser beam 3 is one-dimensionally deflected by the galvanometer mirror 8 and by a plane reflection mirror 9 onto the phosphor sheet 1. Transport means, not shown, are provided to transport the sheet in the direction of the arrow 11, to enable the whole sheet to be scanned in a uniform manner.

Positioned closed to, but behind the scanning line of the laser beam 3 on the phosphor sheet 1, is a light guide 12 which receives light emitted from the phosphor sheet 1 but is shielded from direct exposure to the laser beam 3. The light guide 12 consists of individual optical fibers that are bundled at the output end. The output end of the light guide is positioned adjacent a photo-detector 13, which produces an electrical signal dependent upon the light intensity falling thereon.

Suitable electric connections are made to pass the output signal from the photo-detector 13 to a computer 20 which serves to control the light chopper 4 and the galvanometer mirror drive 6 and to perform the method of the present invention as well as other kinds of image processing techniques on the output signal.

The output of the computer is additionally connected to a display unit 21, such as a VDU screen. Alternatively or additionally the output of the computer 20 is used to produce a permanent record of the image. The output can also be fed to a workstation for off-line processing and/or to an archive station etc. (not shown).

The read-out signal obtained at the output of the photo-detector 13 was fed to a square root amplifier 30 where it was amplified. It was then sampled by a sample and hold circuit 31, and converted into a 12 bit signal by means of an analog to digital convertor 32.

A shading correction 40 was then applied to the read-out signal by multiplying each pixel value with an appropriate correction value determined in advance.

The digital signals thus obtained were sent via switch 33 either to a section 34 where correction values were calculated according to the method of the present invention, or to a noise reducing correction section 36 where a read-out signal was corrected using these correction values.

The procedure for calculating correction values is as follows.

Before read-out of actual diagnostic images was performed, each screen that was to be used in the read-out apparatus was subjected to a uniform flat-field exposure (in the absence of any patient or X-ray modulating object).

The uniformly exposed screens were then consecutively fed into the read-out apparatus for identification and read-out.

Identification was performed by reading the identification information stored in an electronic memory (an EEPROM) provided on the cassette conveying the photostimulable phosphor screen.

Image read-out was performed following the method described higher.

The read-out signals were then subjected to square root amplification, sampled and converted into a digital signal as has been described higher.

The digital signals were then applied via switch 33 to the correction value calculation circuit 34 where for each individual pixel of a screen a corresponding correction value was calculated as will be explained extensively below.

Then, the matrix of correction values for each pixel in a screen, in the following called a calibration matrix, was stored in memory 35 together with the associated identification item. Typically about 30 different photostimulable phosphor screens are used in a single read-out apparatus.

This procedure was performed for every photostimulable phosphor screen that was to be used in the read-out apparatus.

Instead of storing calibration matrices, one could perform the procedure of determining a calibration matrix before every exposure of a recording member to a radiation image. Although being extremely accurate, this procedure would be highly time-consuming.

It is also possible to perform the procedure according to the present invention only for these photostimulable phosphor screens that are used for specific examination types such as e.g. mammography in which confusing of e.g. microcalcification with a defect on a recording member could easily occur. This would have detrimendous effects on the diagnosis.

During normal use of the screens, a radiation image (of a patient or of an object) stored in a specific screen was identified and read-out and the digital image signals representing the radiation image were fed via switch 33 to correction circuit 36.

The noise reduction circuit then retrieves from memory 35 the correction values pertaining to the identified screen and carries out correction by addition or multiplication of read-out pixel values with/or the corresponding correction values.

Next, the corrected signal was applied to a processing circuit 37 where it was further subjected to various kinds of processing such as frequency and gradation processing etc. which methods fall out of the context of the present application.

Finally a hard or soft copy image was generated on an output device 38 (a hard copy recorder, display unit etc . . . ).

Figure 3A:
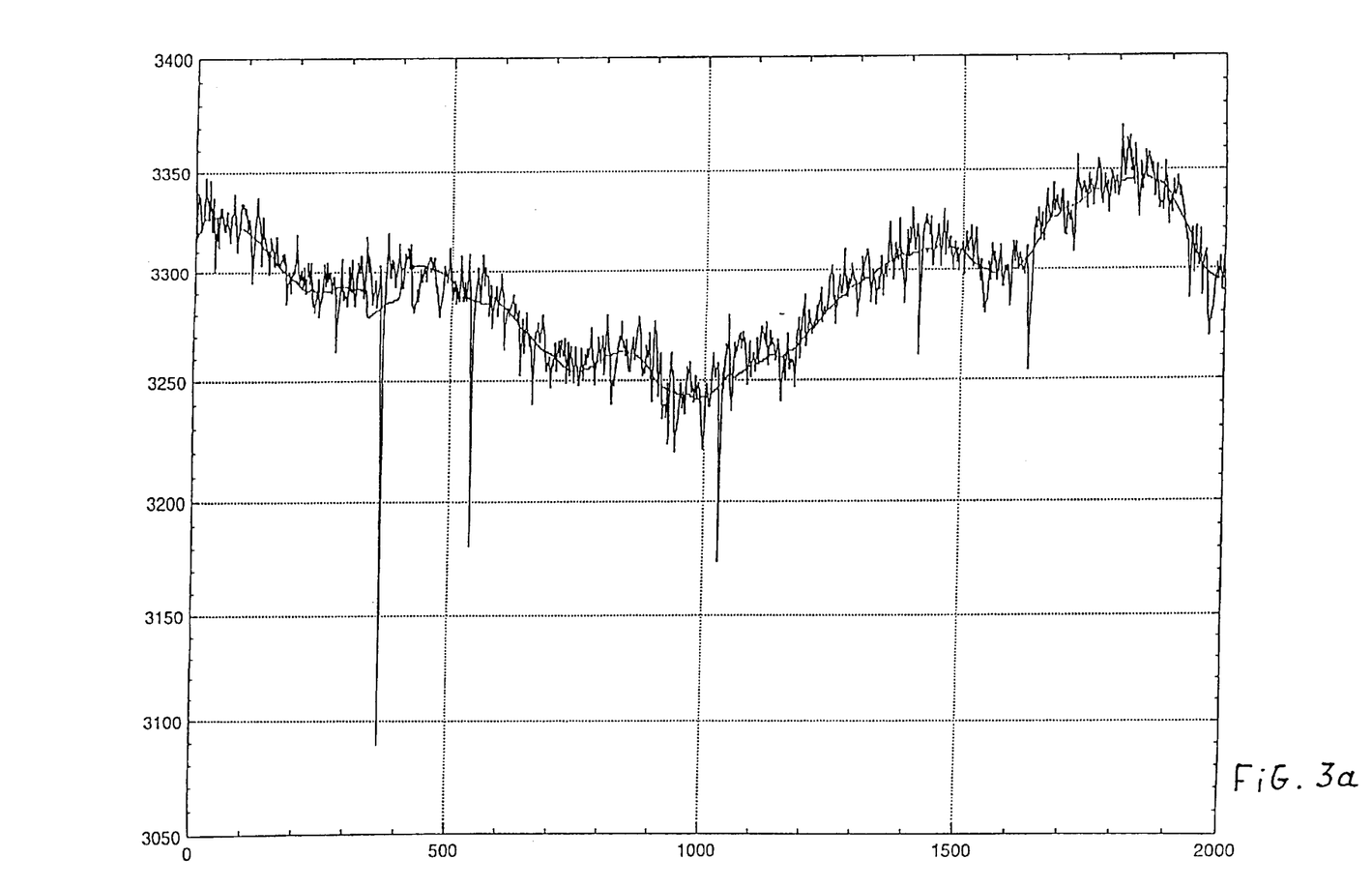
FIG. 3a depicts a typical scan line of a stimulable phosphor screen subjected to a flat field exposure.
Figure 3B:
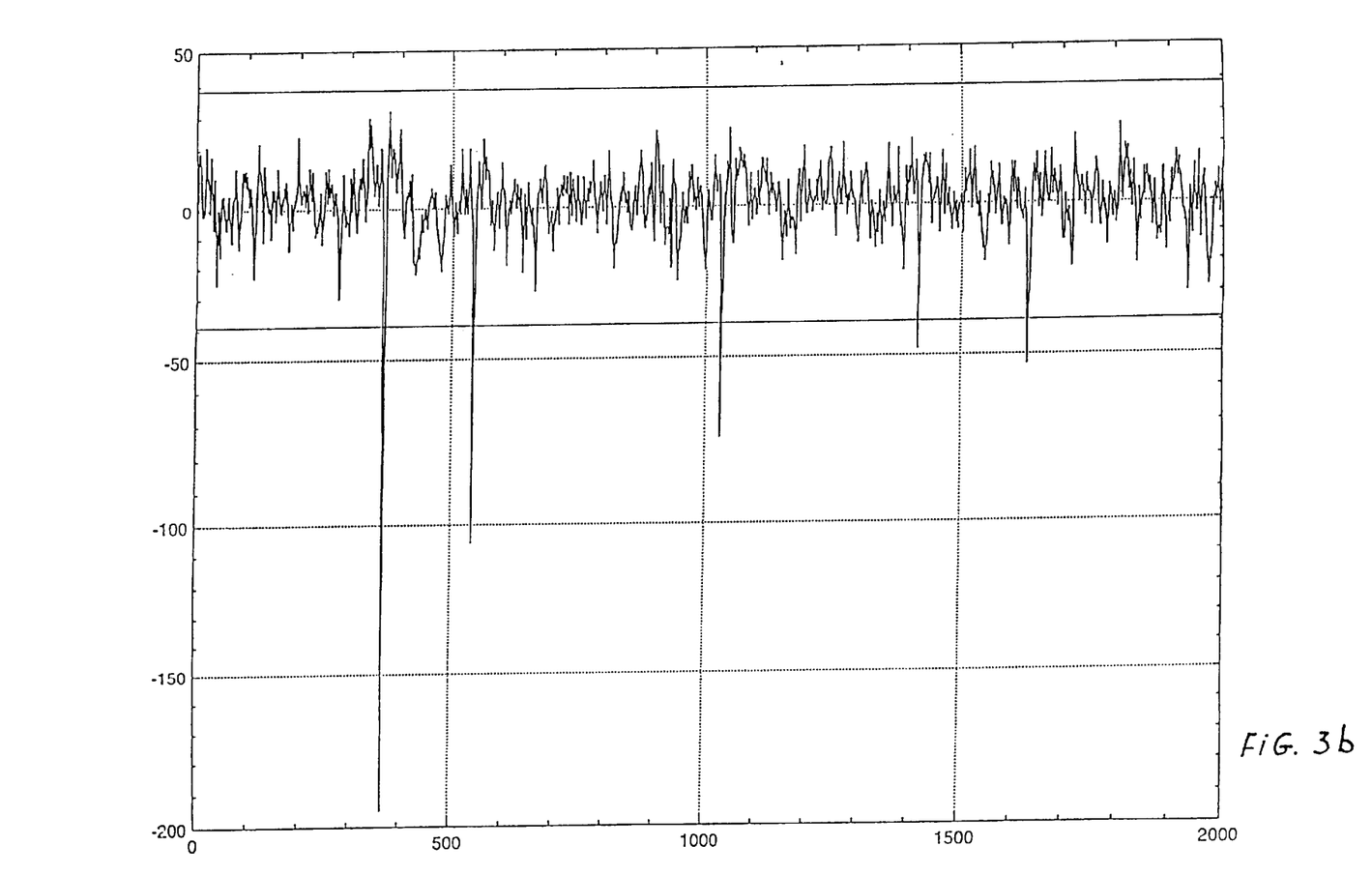
FIG. 3b shows the same scan line having been subjected to background removal.
Figure 3C:
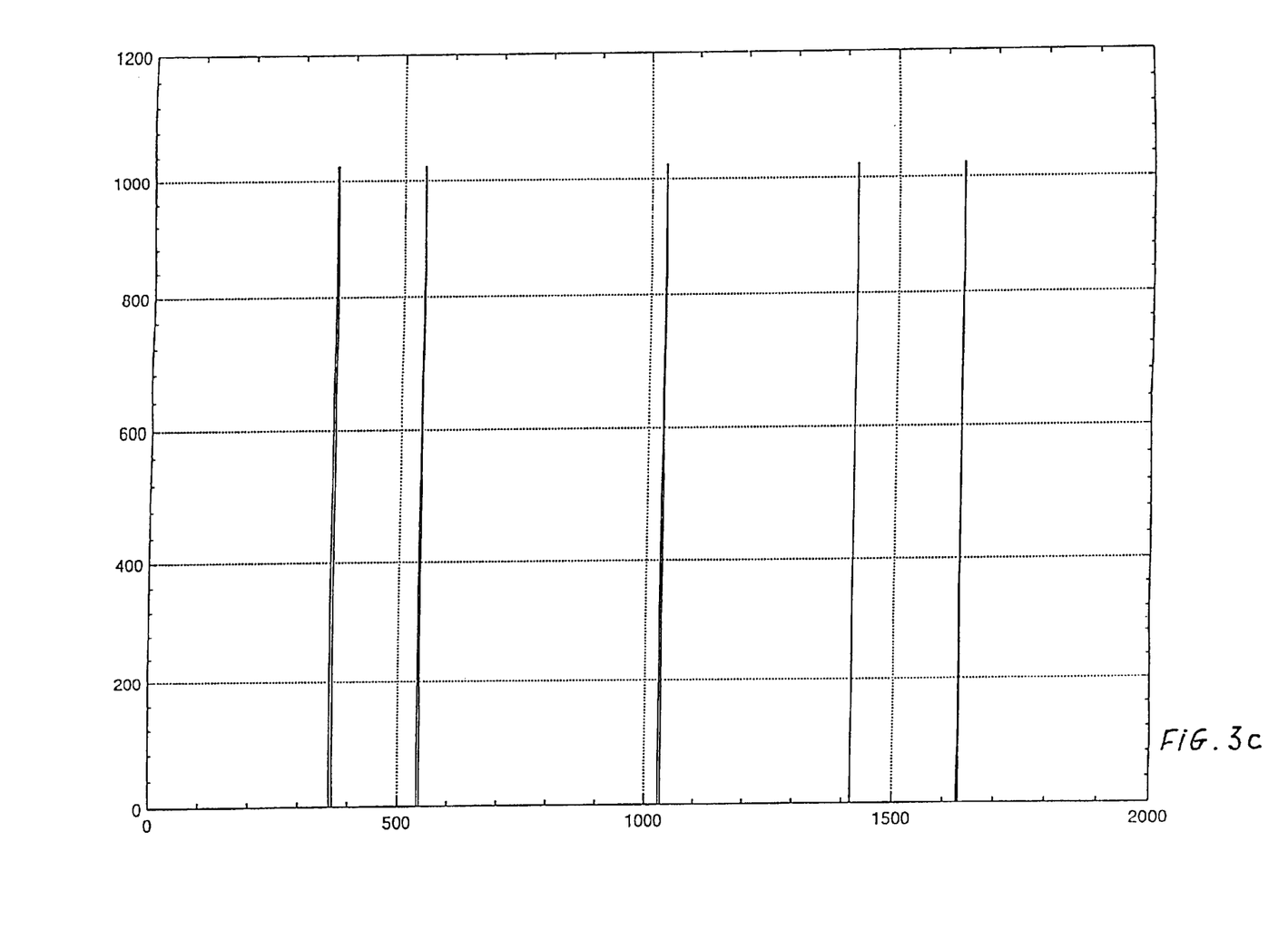
FIG. 3c shows the result of a thresholding operation performed on the scan line of FIG. 3b.

As will be explained below, local defects that are detected after background removal are threshold with a floating threshold value T in circuit 34 (see FIGS. 3b and 3c). The result of this thresholding operation is a digital overlay image (bit map image) which is stored in memory 35 and retrieved at the time an actual image stored in an identified photostimulable phosphor screen is corrected.

The digital overlay image is applied to a hard copy recorder 38 for the production of an overlay image which represents defective area as coloured regions or contours. The overlay image is superimposed by the radiologist on the hard copy or soft copy of the actual radiographic image so that he is informed of the location of such local defects and will not confuse these defects with elements that are relevant with regard to the diagnosis.

The digital overlay image is further applied to a characterisation and classification circuit 39 wherein the defects are classified according to a number of characteristics as explained in detail furtheron.

In this way a quality report of the recording member can be created and output. On the basis of this report acceptance or rejectance of a recording member can be decided.

The steps of the method of the present invention that have been described in general will be explained below in more detail. First a number of procedures are explained for calculating the background image $g_R(i,j)$ used for generating a calibration matrix.

4.1. Modeling of the defectless recording member

When the recording member is exposed to a flat field exposure, the signal is ideally expected to be a constant with noise superimposed. The noise consists of Poisson distributed quantum noise, dependent on X-ray exposure and fixed structured noise, independent of X-ray exposure. At moderate amount of exposure, the first noise source dominates, and by subsequent square root compression, it can be modelled as independent additive Gaussian noise with predictable standard deviation. The signal is thus ideally composed of a spatially constant mean value with signal independent additive noise.

As enumerated in the foregoing, the ideal model is distorted according to a variety of defect sources. FIG. 3a depicts a typical scan line of a stimulated phosphor subjected to a flat field exposure. In contrast to being a constant, it shows a slowly varying background immersed in noise. The defectless member is characterized by deriving an analytical or discrete function representing the background latitude.

Several methods have been tested to model the background. They are either analytical or empirical in nature but all have in common that they are level-based methods and will entail level-based defect detection. The sequel shortly describes these methods.

4.1.1. Global 1- and 2-dimensional regression

Regression is a widely employed technique and ready-to-use implementations are available such as presented in Press. W. H. et al., Numerical Recipes in C, 2nd Edition, Cambridge University Press, 1992, Chapter 15: Modeling of Data. Regression is a method where the N=K.L data points, in casu the 2-dimensional array of gray values, are fitted to a model that has M adjustable parameters $a_j$, j=1 ... M. By the qualifier 'global' is meant that the spatial extent of the data covers the complete image, that is K and L denote the image dimensions. The error minimized is the least-squares error $$\sum_{i=1}^{K} \sum_{j=1}^{L} \left( \frac{z_{i,j} - z(i,j;a_1 \ldots a_M)}{\sigma(i,j)} \right)^2$$

where the $z_{i,j}$ denote the actual gray values, $z(i,j; a_1, \ldots a_M)$ denote the functional relationship between independent and dependent variables and the $\sigma_{i,j}$ are the standard deviation of the measurement error on $z_{i,j}$. Least squares fitting is a maximum likelihood estimation of the fitted parameters when the $\sigma_{i,j}$ are constant. This maximum likelihood estimate amounts to a chi-square fitting when $\sigma_{i,j}$ are non-constant and supplied for each gray value. By taking the derivative with respect to the parameters $a_k$, we obtain equations that must hold at the chi-square minimum, $$0 = \sum_{i=1}^{K} \sum_{j=1}^{L} \left( \frac{z_{i,j} - z(i,j)}{\sigma_{i,j}^2} \right) \left( \frac{\delta_z(i,j; \ldots a_k \ldots)}{\delta a_k} \right) \quad k = 1, \ldots, M$$

This is in general a set of M nonlinear equations for the M unknown $a_k$.

The solution of the system of equations becomes mathematically more tractable when the model is a linear combination of any M specified functions of the spatial coordinates i,j. This kind of regression is termed as general linear least squares and has the following form of the model $$z(i,j) = \sum_{k=1}^{M} a_k Z_k(i,j)$$

where the basis functions $Z_1(i,j) \ldots, Z_M(i,j)$ are arbitrary fixed functions (but possibly non-linear functions of the spatial coordinates x,y). The computation has further been speeded up considerably by randomly sampling a fraction of the total number of data points in the image plane either by using random number generators or by quasi-random number generators such as Sobol' sequences, introduced in e.g. H. Press et al., Numerical Recipes in C, Cambridge University Press, 1992, Chapter 7: Random Numbers.

A special case has been tested using polynomials as the basis functions. It is easily conceivable that any other suitable basis functions could be used without departing from the general principle of least squares fitting. By way of example, but not restricted to it, the polynomial up to exponential degree 4 has the following form $$z(x,y) = a_1 + a_2 x + a_3 y + a_4 x^2 + a_5 y^2 + a_6 xy + a_7 x^2 y + a_8 xy^2 + a_9 x^2 y^2$$

representing a case with M=9.

In a further refinement to speed up computation without compromising accuracy, the model of the background gray value variation has been simplified to the pure one-dimensional case, whereby each scan line is modelled as a polynomial of degree M−1:

$$z(x,y) = a_1 a_2 x + a_3 x^2 + \ldots + a_M x^{M-1}$$

Again here, the basis functions can be any linear or non-linear function of the place domain coordinates.

4.1.2. Local 1- and 2-dimensional spline fitting

The picture can be thought of as a surface by using the brightness value as the third coordinate. The surface can be too complex however to be described by a single equation over the domain of the image, such as computed by global regression, and therefore the need for piecewise approximation arises. Such piecewise representation is offered by splines such as presented in T. Pavlidis, Algorithms for graphics and image processing, Computer Science Press, 1982, Chapter 11 Curve fitting with splines, Chapter 12 Approximation of curves and Chapter 13 Surface fitting. According to the nature of representation, splines can be subdivided into either interpolating or approximating, having either fixed knots or variable knots. Subdividing the image into tiles of equal size (200×200 pixels), the fitting problem belongs to the class of approximating splines with fixed knots. Knots (or control points) are held fixed here, since increasing the number of knots in areas of higher local variance is undesirable, precisely because they may represent defects.

In contrast to the discrete methods used hereafter, the analytical representation enables much more compact storage of the calibration matrix, to be defined next. Instead of storing the individual additive or multiplicative correction coefficient for each pixel, the coefficients of the approximating splines are stored. The actual background values are reconstructed at the time of processing the image. Although the storage capacity needed and the computation time required for spline fitting are larger than those of the global regression method, the benefit offered by splines is that they can more accurately model the background variation. The computation has been speeded up in an alternative implementation by computing the approximating splines for successive one-dimensional scan line profiles.

4.1.3. Background determination by smoothing

The former methods are analytical, that is, they express the background as a linear combination of analytical functions. A discrete representation offers the advantage that no prior knowledge as to the nature of the background variation is required, so they can handle much more complex variation. On the other hand, the storage capacity needed for each calibration matrix is proportional to the number of pixels. A local discrete approximation of the gray value surface can be obtained by smoothing with a smoothing kernel of appropriate size. The values of the coefficients of the smoothing kernel are well documented in the open literature and can typically represent a box filter with constant coefficients or a filter with coefficients derived from a gaussian: W. K. Pratt, Digital Image Processing, 2nd ed., Wiley Interscience. These kernels are separable and can be obtained by successive horizontal and vertical convolution. The box filter has the additional property that it was implemented in a recursive way, using the previous smoothed value, and one addition and one subtraction per direction and per pixel. Smoothing filters are convolutions and can also be obtained by multiplication with the kernel's transfer function in the Fourier domain.

Formulas implemented 2 dimensional convolution with an odd-size $(2M+1) \times (2N+1)$ kernel $$\bar{z}(x,y) = \sum_{m=-M}^{M} \sum_{n=-N}^{N} h(m,n) z(x-m, y-n)$$

with $$h(m,n) = \frac{1}{(2M+1)(2N+1)} \begin{bmatrix} 1 & 1 & 1 & \ldots & 1 \\ 1 & \ldots & & & \\ 1 & & & & \\ \vdots & & & & \\ 1 & 1 & 1 & \ldots & 1 \end{bmatrix}$$

for the box filter and $$h(m,n) = A \exp\left(-\frac{m^2+n^2}{2\sigma^2}\right) \text{ with } A \text{ such that } \sum_{m=-M}^{M} \sum_{n=-N}^{N} h(m,n) = 1$$

for the gaussianly shaped filter. Typical size used is M=N= 65.

Separable implementation on rows and columns $$r(x,y) = \sum_{m=-M}^{M} h_r(m) z(x-m, y)$$

$$\bar{z}(x,y) = c(x,y) = \sum_{n=-N}^{N} h_c(n) r(x, y-n)$$

-continued with $$h_r(m) = \left(\frac{1}{2M+1}\right) [1 \, 1 \ldots 1]$$

$$h_c(m) = \left(\frac{1}{2N+1}\right) [1 \, 1 \ldots 1]$$

for the box filter and $$h_r(m) = A_r \exp\left(-\frac{m^2}{2\sigma^2}\right)$$

$$h_c(n) = A_c \exp\left(-\frac{n^2}{2\sigma^2}\right)$$

for the gaussianly shaped filter with $A_r$ and $A_c$ such that $$\sum_{m=-M}^{M} \sum_{n=-N}^{N} h(m,n) = 1.$$

For $M = N$, $A_r = A_c = \sqrt{A}$.

Recursive and separable box smoothing implementation after initialization $$r(x,y)=r(x-1,y)+z(x+M,y)-z(x-M-1,y) \; \bar{z}(x,y)=c(x,y)=c(x,y-1)+r(x,y+N)-r(x,y-N-1)$$

Figure 4:
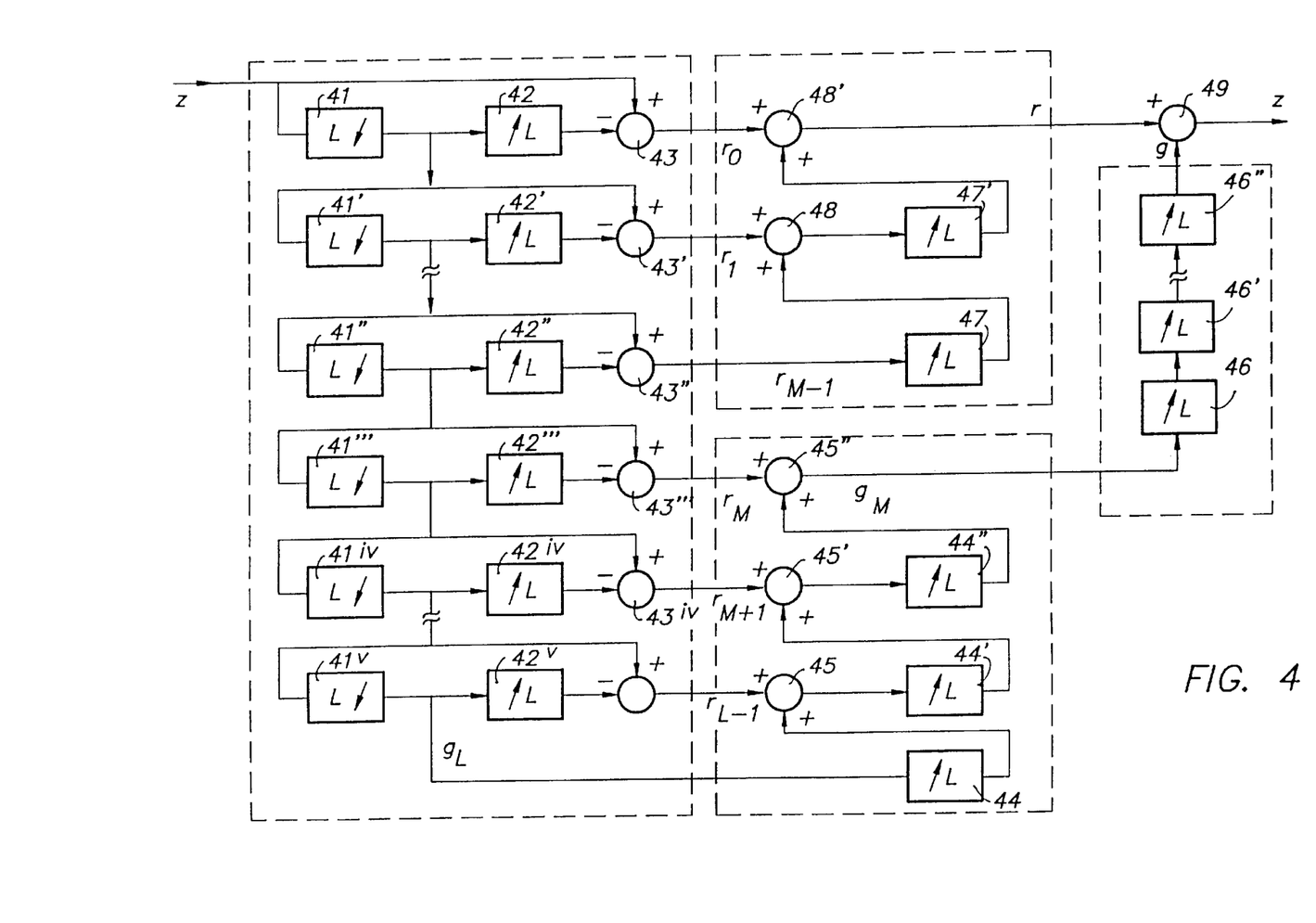
FIG. 4 depicts a particular embodiment of a hierarchical multi-resolution image decomposition method and the generation of a background image starting from the decomposed image.
Figure 5:
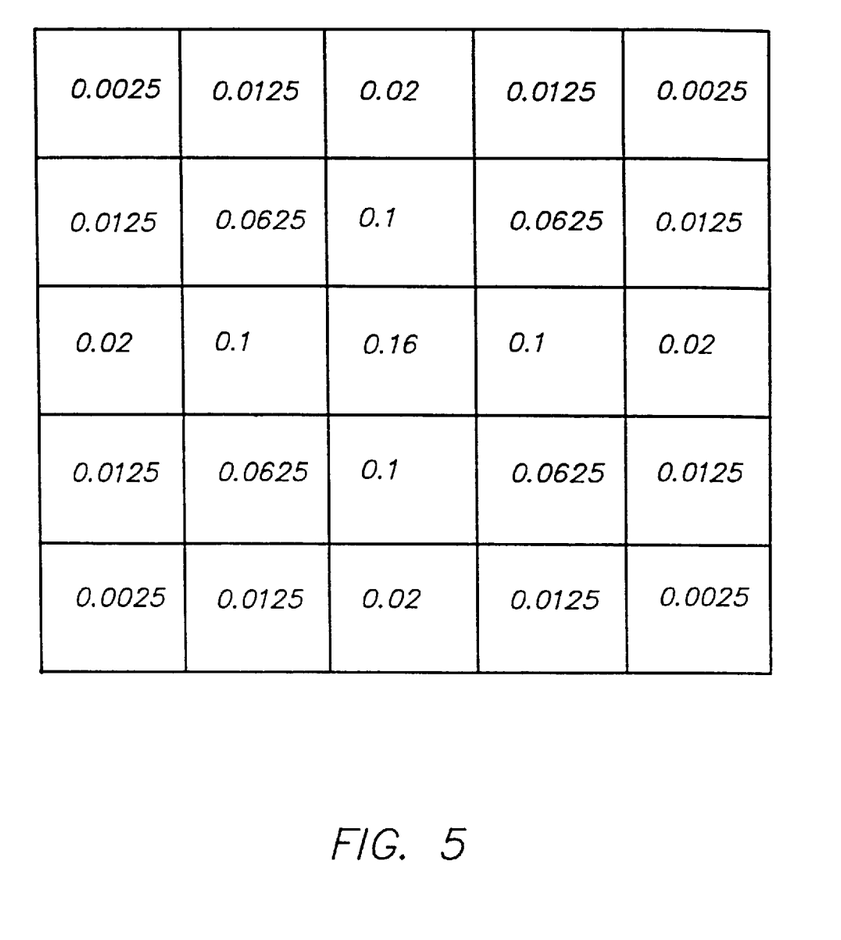
FIG. 5 shows an example of a filter used in said decomposition method.

4.1.4. Background determination by hierarchical decomposition and reconstruction A common framework for both local and global distortion modeling on a discrete grid, is obtained by a pyramidal decomposition and reconstruction such as disclosed in EP 0 527 525. A preferred embodiment of the decomposition process is depicted in FIG. 4. The original image z(i,j) is filtered by means of a low pass filter 41, and subsampled by a factor of two, which is implemented by computing the resulting low resolution approximation image $g_1$ only at every other pixel position of every alternate row. A detail image $r_0$ at the finest level is obtained by interpolating the low resolution approximation $g_1$ with doubling of the number of rows and columns, and pixelwise subtracting the interpolated image from the original image z. The interpolation is effectuated by the interpolator 42, which inserts a column of zero values every other column, and a row of zero values every other row respectively, and next convolves the extended image with a low pass filter. The subtraction is done by the adder 43. The same process is repeated on the low resolution approximation $g_1$ instead of the original image z, yielding an approximation of still lower resolution $g_2$ and a detail image $r_1$. A sequence of detail images $r_i$, i=0 . . . L−1 and a low resolution approximation $g_L$ are obtained by iterating the above process L times. The finest detail image $r_0$ has the same size as the original image. The next coarser detail image $r_1$ has only half as many rows and columns as the first detail image $r_0$. At each step of the iteration the maximal spatial frequency of the resulting detail image is only half that of the previous finer detail image, and also the number of rows and columns is halved, in accordance with the Nyquist criterion. After the last iteration an image $g_L$ is left which can be considered to be a very low resolution approximation of the original image. In the extreme case it consists of only 1 pixel which represents the average value of the original image z. The filter coefficients of the low pass filter of the preferred embodiment are presented in FIG. 5. They correspond approximately to the samples of a two-dimensional gaussian distribution on a 5×5 grid. The same filter coefficients are used for the low pass filters 41,41', . . . , 41''' at all scales. The same filter kernel with all coefficients multiplied by 4 is also used within the interpolators 42,42', . . . , 42'''. The factor 4 compensates for the insertion of zero pixel columns and rows as explained above.

A decomposition of the original image z consisting of a background g and a residual component r $$z(i,j)=g(i,j)+r(i,j)$$

is depicted in FIG. 4. Each of g and r is obtained by reconstruction using the appropriate subset of pyramid levels, as explained next.

The background image g is obtained by reconstruction using the lowest resolution levels. The coarsest resolution image $g_L$ is first interpolated by interpolator 44 to twice its original size and the interpolated image is next pixelwise added to the image of the next coarsest level $r_{L-1}$ using adder 45. The resulting image is interpolated and added to the next finer detail image. If this process is iterated L–M times using the unmodified resolution levels $r_{L-1}, \ldots, r_M$, then a low resolution background image $g_M$ will result. This image is blown up to the size of the original image z by means of the interpolators 46,46',46'', to yield background image g. If M=L, and the detail images $r_{L-1}, \ldots, r_M$ are left unmodified, the original image z will result by this reconstruction process.

The residual or error image is obtained by reconstruction using the highest resolution levels. Starting from resolution level M, the detail image $r_{M-1}$ is interpolated by interpolator 47 to twice its original size and the interpolated image is next pixelwise added to the image of the next finer detail level $r_{M-2}$ in adder 48. The resulting image is interpolated and added to the next finer detail image. If this process is iterated M times using the unmodified resolution levels $r_{M-1}, \ldots, r_0$, then a full resolution residual or error image r is obtained.

Obviously, r and g need not be computed simultaneously: either g is computed and r can be obtained in a straightforward manner as r=z–g, or r is computed and g can be obtained as g=z–r by image subtraction.

4.2. Modeling and detection of the defects

To the purpose of detecting defects on a recording member, the recording member is exposed to a flat field exposure, which ideally yield a constant signal amplitude referred to as the background image. The defects can be modelled as artefact-like shaped signals superimposed on the background variation immersed in noise. The point defects are peaks of small support in both directions. Their amplitude exceeds the peak-to-peak range of the noise. Line defects coming from scratches and traces have one of their dimensions substantially larger than the other. Their cross-profile exhibits a peak-like form. Area defects introduce global deviation from a constant signal and represent variations with wider extent and therefore need global correction. Since point and line defects have at least one substantially smaller dimension, and hence have low area, the background image is only slightly affected by the presence of the defects. This property enables the computed background approximation to pass through the defects, without actually being disturbed by them, and hence point and level defects produce sufficient residual level signal. Area defects on the other hand do affect the parameters of the analytical approximation methods and distort the shape of the surface obtained by discrete or analytical approximation methods, hence the calibration matrices derived will correct for them in the actual image, what should be achieved.

4.2.1. Local defect detection

In view of the fact that the background variation is not constant, global thresholding is not straightforwardly applicable. The threshold should be floating as a function of background variation, or alternatively accomplished after background removal. Irrespective of which of the former methods is used to approximate the background, background removal is generally accomplished by the following equation to yield the residual signal:

$$r(i,j)=z(i,j)-\bar{z}(i,j)$$

in which $\bar{z}(i,j)$ is a background fitted signal obtained by one of the formerly described methods. A defectless error signal has zero mean $\mu_r$ and known noise variance $\sigma_r$. Peaks resulting from defects will be superimposed and can be detected by thresholding the absolute value $|r(i,j)|$ with a noise dependent threshold T $$e(i,j)=1 \text{ if } |r(i,j)|>T=0$$

elsewhere $$T=\alpha\sigma_r$$

and $\alpha$ typically in the range 3 . . . 5. For gaussianly distributed noise $N(\mu,\sigma)$, 99.9% of all gray values will lie in the 3-$\sigma$ range around the mean value $\mu$. Any deviation larger than the noise-dependent threshold is attributed to defects.

4.2.2. Global defect correction

Figure 6:
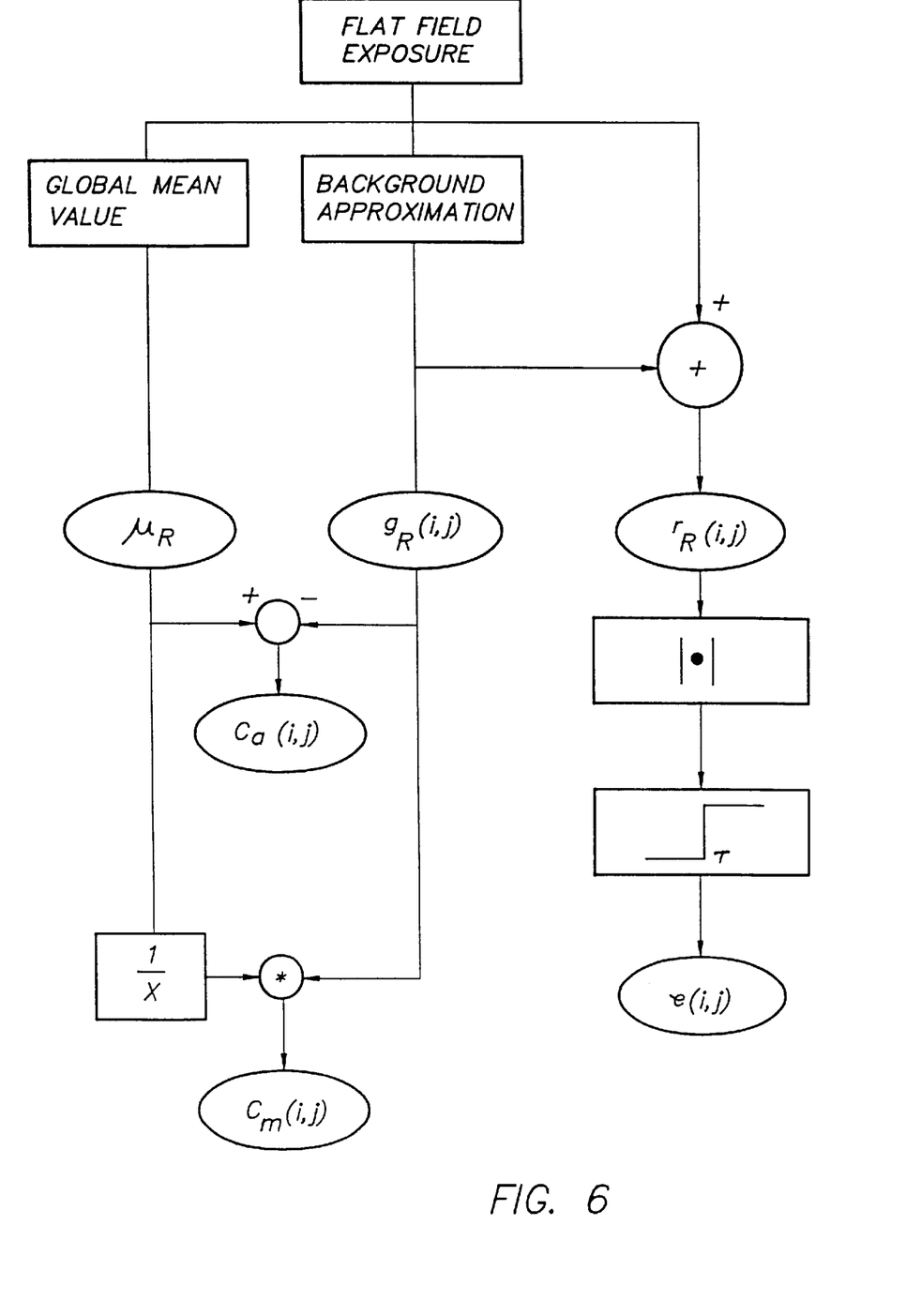
FIG. 6 illustrates the calibration matrix computation and the error detection.

The availability of either an analytical model or an empirically derived background surface enables the establishment of a two-dimensional calibration matrix to correct for global distortions. By global distortion is meant any deviation on the recording means with sufficiently large extent w.r.t. the image dimensions. This extent relates to the size of the smoothing kernel for empirical background fitting methods and to the shape of the basis functions for the analytical approximation methods. The correction is done in either an additive or a multiplicative manner. An additive calibration matrix $C_a(i,j)$ (see FIG. 6) is constructed by computing the pixelwise offset between the smooth background image $g_R(i,j)$ and the global mean value $\mu_R$ of the reference image obtained by a flat field exposure of the recording member $$C_a(i,j)=\mu_R-g_R(i,j)$$

Alternatively, a multiplicative correction matrix $C_m(i,j)$ is computed (see FIG. 6) as the ratio of mean value $\mu_R$ and the smooth background variation $g_R(i,j)$ $$C_m(i,j) = \frac{\mu_R}{g_R(i,j)}$$

Figure 7:
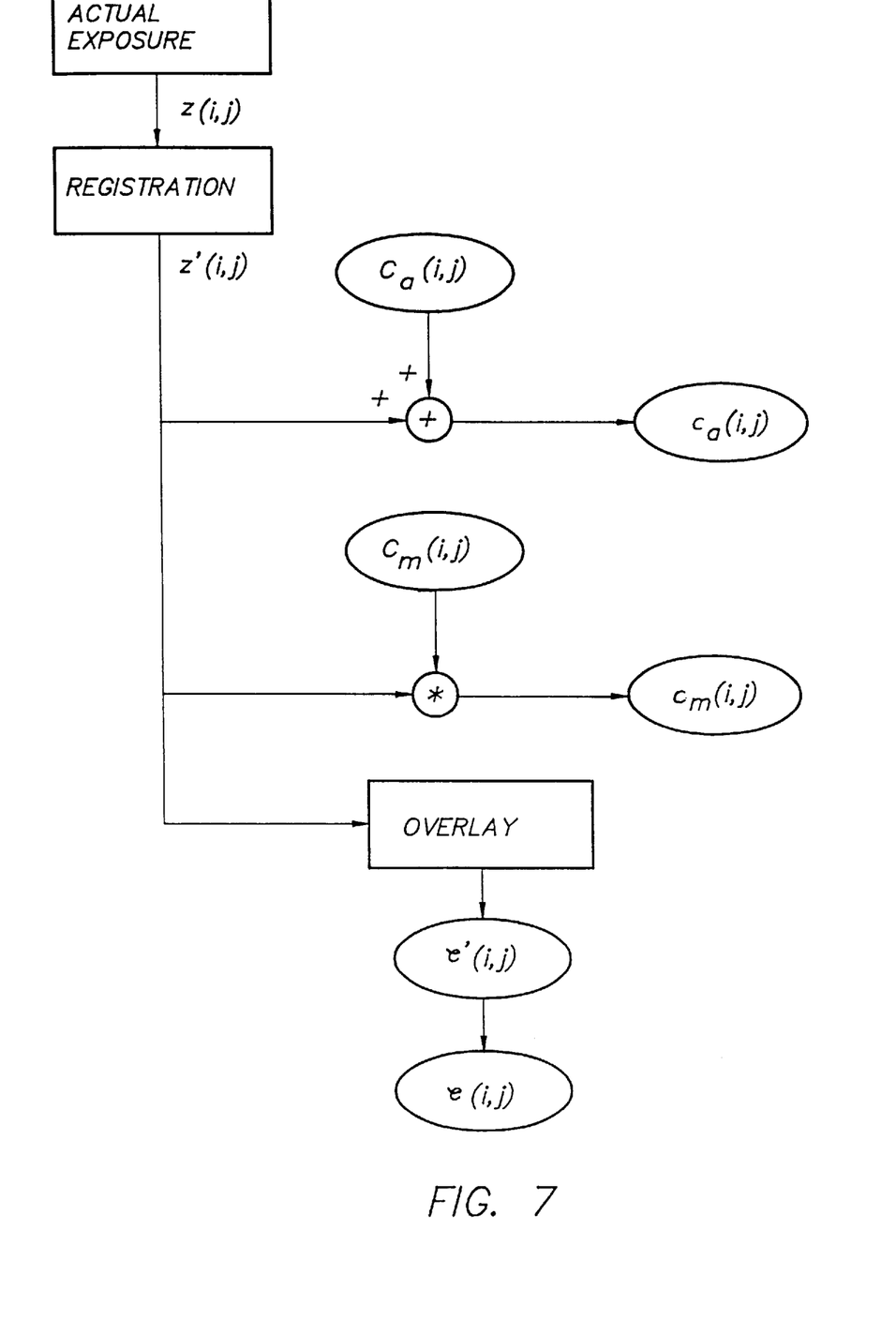
FIG. 7 illustrates the correction of an actual image.

Application of the calibration matrices to an actual exposure as shown in FIG. 7 will undo any global variation w.r.t. the mean value due to recording member deficiencies.

Calibration of the actual image using the calibration matrix requires both images be registered. Registration of two images taken at different exposure and read-out times and representing physically different objects, requires the use of landmarks or fiducial markers during exposure. We have used prior art for the registration problem such as reported in Y. Christophe, J. Cornelis, P. De Muynck, Subpixel geometric correction of digital images, Signal Processing IV, Proc. of EUSCIPCO 1988, Vol. 3, pp 1605–1608. Detection and location to subpixel accuracy of landmarks, enables the establishment of a coordinate system for the actual and the reference image. An affine transformation matrix is computed, transforming the coordinate system of the actual image to the coordinate system of the reference or calibration image. Next, the calibration image and diagnostic image are brought into correspondence by applying the affine transformation to the actual image z(i,j) to yield the geometrically transformed image z'(i,j). Pixel values at non-integer coordinates are obtained by bi-linear interpolation. Other interpolation schemes could be envisaged.

A global additive correction is performed by adding to the registered image z'(i,j) the correction matrix $C_a$(i,j) or alternatively stated, by adding a pixel dependent offset $C_a$(i,j) to the image z'(i,j), with R denoting the reference or calibration image:

$$C_a(i,j)=z'(i,j)+C_a(i,j)=z'(i,j)+(\mu_R-g_R(i,j)).$$

The multiplicative correction is performed by multiplying the registered image z'(i,j) with a pixel dependent correction factor $C_m$(i,j)

$$c_m(i,j) = z'(i,j) \cdot C_m(i,j) = z'(i,j) \cdot \left( \frac{\mu_R}{g_R(i,j)} \right)$$

4.3. Postprocessing

The result local defect detection by thresholding the residual or error image is a binary image, in which 1 denotes a defect (foreground) pixel, 0 denotes a background pixel. Spurious false alarms with small, user defined size can be removed by successive erosions of the foreground. The original thickness or remaining defects can be restored by an equal amount of dilations. The shape of the planar mask used was a 3×3 square mask.

Other morphological processing could be envisaged such as presented in A. K. Jain, Fundamentals of Digital Image Processing, Prentice Hall, 1989, p.384 to preserve specific shapes of defects such as lines.

4.4. Overlay construction

For the purpose of signalling critical areas to the operator, requiring his specific attention, an overlay image (see FIG. 6) is constructed, representing possible defective zones detected in the previous stages. The overlay image represents the defective zones either as coloured regions or as countours.

4.4. Characterization and classification of the defects

The availability of a bitmap image representing the defective pixels enables characterization and automatic classification of the defects as either point-like, line-like or area like. For the purpose of shape characterization, shape features have been computed such as documented in (1) A. K. Jain, Fundamentals of image processing, Prentice Hall, 1989, p. 390, Shape features; (2) W. K. Pratt, Digital Image Processing, 2nd ed., Wiley, p. 629, Shape analysis. Features of each of the connected components are computed. Geometric features include perimeter, area, minimum and maximum radii, Euler number, corners on curved like defects, compactness, symmetry. Moment based features include center of mass, orientation, bounding rectangle, best fit ellipses and eccentricity. Features based on Fourier descriptors of the contour are derived from the amplitudes and phases of the Fourier coefficients. Other descriptors could be envisaged as well. Classification techniques well known in the art such as statistical or neural classifiers have been used to classify a defective region as either a point, a line or an area defect. The severity of a potential defect is further assessed by examining the ratio of the amplitude of the defect signal with respect to the local background gray value. Based on shape and amplitude of the defects, the recording member finally is either definitely accepted for use, marginally accepted or rejected.

I claim:

1. Method of correcting a radiation image stored in a recording member for recording member defects, comprising:

generating a calibration matrix for said recording member, said calibration matrix comprising for each pixel on said recording member a correction value that represents a deviation of a first value that is effectively obtained in a pixel and a second value that would be expected when said recording member is subjected to a flat field exposure and subsequently read-out by means of a calibrated read-out system, generating a digital signal representation of said radiation image by reading the image by means of a calibrated read-out system, correcting each pixel of said radiation image by applying to a pixel a corresponding value of said calibration matrix.

2. A method according to claim 1 wherein said calibration matrix is generated in advance, stored in memory and retrieved upon identification of a recording member.

3. A method according to claim 1 wherein (i) said recording member is a photostimulable phosphor screen and wherein (ii) a radiation image is read-out by scanning said screen by means of stimulating radiation, detecting light emitted upon stimulation, converting detected light into an electric signal and digitizing said signal.

4. A method according to claim 1 wherein (i) said calibration matrix is obtained by exposing said recording member to a flat field exposure of radiation, reading a flat field image stored in the recording member exposed to said flat field exposure, calculating a global mean value $\mu_R$ by averaging pixel values of said flat field image, generating a smooth background image $g_R$(i,j) as $\mu_R - g_R$(i,j), and (ii) each pixel of said radiation image is corrected by adding to a pixel a corresponding value of the calibration matrix.

5. A method according to claim 4 wherein said smooth background image $g_R$(i,j) is obtained by applying a regression technique to pixel values of said flat field image.

6. A method according to claim 4 wherein said smooth background image $g_R$(i,j) is obtained by smoothing pixel values of said flat field image.

7. A method according to claim 4 wherein said digital signal representation of original image 'z' is decomposed into a sequence of detail images $r_1, r_2 \ldots r_{L-1}$ and a rest image $g_L$ at a still lower resolution level and wherein said residual image 'r' is formed by summing up detail images at M finest resolution levels starting from M−1 up to level 0, each of the detail images being interpolated to the size of a detail image at a next finer resolution level before being summed up.

8. A method according to claim 4 wherein said smooth background image $g_R$(i,j) is obtained by applying a spline fitting technique to pixel values of said flat field image.

9. A method according to claim 4 wherein said digital signal representation of original image 'z' is decomposed into a sequence of detail images $r_1, r_2 \ldots r_{L-1}$ and a rest image $g_L$ at a still lower resolution level and wherein said residual image 'r' is formed by (i) summing the rest image $g_L$ and the detail images $r_i$ at L–M coarsest resolution levels, starting from resolution level L up to resolution level M, each being interpolated to the size of a detail image at a next finer resolution being summed, to form a downzoomed background image $g_M$, (ii) upzooming background image $g_M$ to form a full-size background image 'g' by performing M successive interpolations on $g_M$, (iii) subtracting the upzoomed background image 'g' from the digital signal representation of original image 'z'.

10. A method according to claim 1 wherein (i) said calibration matrix is obtained by exposing said recording member to a flat field exposure of radiation, reading a flat field image stored in the recording member upon said flat field exposure, calculating a global mean value $\mu_R$ by averaging pixel values of said flat field exposure, generating a multiplicative calibration matrix $C_m(i,j)$ as $\mu_R/g_R(i,j)$, and (ii) each pixel of said radiation image is corrected by multiplying a pixel with a corresponding value of the calibration matrix.

11. A method according to claim 10 wherein said smooth background image $g_R(i,j)$ is obtained by applying a regression technique to pixel values of said flat field image.

12. A method according to claim 10 wherein said smooth background image $g_R(i,j)$ is obtained by smoothing pixel values of said flat field image.

13. A method according to claim 10 wherein said smooth background image $g_R(i,j)$ is obtained by applying a spline fitting technique to pixel values of said flat field image.

14. Method of localising local defects in a recording member for recording a radiation image comprising the steps of exposing said recording member to a flat field exposure of radiation, reading a flat field image stored in the recording member upon said flat field exposure, generating a smooth background image $g_R(i,j)$, generating a residual image $r(i,j)$ by subtracting from a pixel value of the flat field image a corresponding value of the smooth background image $g_R(i,j)$, thresholding the absolute value $|r(i,j)|$ of said residual image $r(i,j)$ with a noise dependent threshold T to generate an error image $e(i,j)$ wherein $e(i,j)=1$ if $|r(i,j)|>T$, $e(i,j)=o$ elsewhere, and wherein $T=\alpha\sigma_R$, $\alpha$ being comprised between 3 and 5 and $\sigma_R$ being the variance of the noise distribution in said flat field image.

15. A method according to claim 14 wherein said digital signal representation of original image 'z' is decomposed into a sequence of detail images $r_1, r_2 \ldots r_{L-1}$ and a rest image $g_L$ at a still lower resolution level and wherein said residual image 'r' is formed by summing up detail images at M finest resolution levels starting from M−1 up to level 0, each of the detail images being interpolated to the size of a detail image at a next finer resolution level before being summed up.

16. A method according to claim 14 wherein said smooth background image $g_R(i,j)$ is obtained by smoothing pixel values of said flat field image.

17. A method according to claim 14 wherein said digital signal representation of original image 'z' is decomposed into a sequence of detail images $r_1, r_2 \ldots r_{L-1}$ and a rest image $g_L$ at a still lower resolution level and wherein said residual image 'r' is formed by (i) summing the rest image $g_L$ and the detail images $r_i$ at L–M coarsest resolution levels, starting from resolution level L up to resolution level M, each being interpolated to the size of a detail image at a next finer resolution being summed, to form a downzoomed background image $g_M$, (ii) upzooming background image $g_M$ to form a full-size background image 'g' by performing M successive interpolations on $g_M$, (iii) subtracting the upzoomed background image 'g' from the digital signal representation of original image 'z'.

18. A method according to claim 14 wherein said smooth background image $g_R(i,j)$ is obtained by applying a spline fitting technique to pixel values of said flat field image.

19. A method according to claim 14 wherein said error image $e(i,j)$ is applied to a hard copy recorder to generate an overlay image.

20. A method according to claim 14 wherein said error image $e(i,j)$ is subjected to characterisation and classification to generate a report on shape and amplitude of defects.

21. A method according to claim 14 wherein said smooth background image $g_R(i,j)$ is obtained by applying a regression technique to pixel values of said flat field image.

* * * * *

UNITED STATES PATENT AND TRADEMARK OFFICE
CERTIFICATE OF CORRECTION

PATENT NO. : 5,832,055
DATED : November 3, 1998
INVENTOR(S) : Piet Dewaele

It is certified that error appears in the above-identified patent and that said Letters Patent is hereby corrected as shown below:

Title page, item [30] Foreign Application Priority Data: "96202232" should read -- 96202232.3 --;

Column 7, line 54, In the equation, "$a_1$" should read -- $\alpha_1$ --;

Column 7, line 57, "$z(i,j; a_1, \ldots a_M)$" should read -- $z(i,j; \alpha_1 \ldots \alpha_M)$ --;

Column 7, line 65, "$a_k$," should read -- $\alpha_k$, --;

Column 8, line 7, "$a_k$." should read -- $\alpha_k$. --;

Column 8, lines 57-58, "and ¶Chapter 13" should read -- and Chapter 13 --;

Column 12, line 24, "= 0" should be deleted;

Column 12, line 26, "elsewhere" should read -- = 0 elsewhere --.

Signed and Sealed this

Seventh Day of March, 2000

Attest:

Q. TODD DICKINSON

*Attesting Officer*    *Commissioner of Patents and Trademarks*